(12) United States Patent
Shin et al.

(10) Patent No.: US 11,617,665 B2
(45) Date of Patent: Apr. 4, 2023

(54) HYBRID-TYPE ARTIFICIAL LIMB DEVICE AND CONTROL METHOD THEREFOR

(71) Applicant: KOREA LABOR WELFARE CORPORATION CO., LTD., Ulsan (KR)

(72) Inventors: Hyunjun Shin, Daejeon (KR); Shinki Kim, Seoul (KR); Mankee Jeon, Bucheon-si (KR); Hyeonseok Cho, Incheon (KR); Jong Kwon Kim, Incheon (KR); Jinkuk Park, Suwon-si (KR); Sehoon Park, Bucheon-si (KR); Jongmoon Choi, Seoul (KR); Huitae Lee, Incheon (KR); Jeichung Ryu, Seoul (KR)

(73) Assignee: KOREA LABOR WELFARE CORPORATION CO., LTD., Ulsan (KR)

( * ) Notice: Subject to any disclaimer, the term of this patent is extended or adjusted under 35 U.S.C. 154(b) by 0 days.

(21) Appl. No.: 17/623,944

(22) PCT Filed: Sep. 27, 2019

(86) PCT No.: PCT/KR2019/012560
§ 371 (c)(1),
(2) Date: Dec. 30, 2021

(87) PCT Pub. No.: WO2021/002536
PCT Pub. Date: Jan. 7, 2021

(65) Prior Publication Data
US 2022/0202596 A1 Jun. 30, 2022

(30) Foreign Application Priority Data
Jul. 2, 2019 (KR) .................. 10-2019-0079536

(51) Int. Cl.
*A61F 2/64* (2006.01)
*A61F 2/70* (2006.01)
(Continued)

(52) U.S. Cl.
CPC ............... *A61F 2/64* (2013.01); *A61F 2/70* (2013.01); *A61F 2/74* (2021.08);
(Continued)

(58) Field of Classification Search
CPC ............................................. A61F 2002/6845
See application file for complete search history.

(56) References Cited

U.S. PATENT DOCUMENTS

2012/0283845 A1* 11/2012 Herr ................. A61F 2/6607
623/24
2015/0164660 A1* 6/2015 Will ...................... A61F 2/64
602/26
(Continued)

FOREIGN PATENT DOCUMENTS

JP       07163607 A     6/1995
JP    2014144037 A     8/2014
(Continued)

OTHER PUBLICATIONS

Notice of Allowance (in English and Korean) issued in Korean Patent Application No. 10-2019-0079536, dated Jul. 12, 2021.
(Continued)

*Primary Examiner* — David H Willse
(74) *Attorney, Agent, or Firm* — Harness, Dickey & Pierce, P.L.C.

(57) ABSTRACT

A hybrid artificial limb device is provided. A hybrid artificial limb device according to an exemplary embodiment of the present invention comprises: a joint upper side connection member positioned at the upper side of a knee; a knee joint member connected to the joint upper side connection mem-
(Continued)

ber; and a frame coupled to the knee joint member to be able to perform a pivot rotation, and forming a femoral part. When the frame performs a pivot rotation about the knee joint member, the passive power from the passive driving module and the active power from the active driving module may be selectively or simultaneously provided to the knee joint member.

15 Claims, 15 Drawing Sheets

(51) Int. Cl.
    *A61F 2/74*     (2006.01)
    *A61F 2/50*     (2006.01)
    *A61F 2/68*     (2006.01)
    *A61F 2/76*     (2006.01)

(52) U.S. Cl.
    CPC ............... *A61F 2002/5003* (2013.01); *A61F 2002/5006* (2013.01); *A61F 2002/5036* (2013.01); *A61F 2002/5038* (2013.01); *A61F 2002/6845* (2013.01); *A61F 2002/701* (2013.01); *A61F 2002/704* (2013.01); *A61F 2002/7625* (2013.01)

(56) References Cited

U.S. PATENT DOCUMENTS

2016/0158029 A1*   6/2016   Kuiken .................... A61F 2/64
                                                                   623/24
2019/0142680 A1     5/2019   Park et al.

FOREIGN PATENT DOCUMENTS

| KR | 1020060039970 A | 5/2006 |
| KR | 20150137426 A | 12/2015 |
| KR | 101932343 B1 | 12/2018 |
| KR | 101947267 B1 | 2/2019 |
| KR | 1020190055598 A | 5/2019 |

OTHER PUBLICATIONS

Written Opinion (in English and Korean) issued in Korean Patent Application No. 10-2019-0079536, dated Jan. 19, 2021.
International Search Report (in English and Korean) and Written Opinion of the ISA (in Korean) issued in PCT/KR2019/012560, dated Apr. 2, 2020; ISA/KR.

* cited by examiner

HYBRID-TYPE ARTIFICIAL LIMB DEVICE AND CONTROL METHOD THEREFOR

CROSS-REFERENCE TO RELATED APPLICATIONS

This application is a U.S. National Phase Application under 35 U.S.C. 371 of International Application No. PCT/KR2019/012560, filed on Sep. 27, 2019, which claims priority to and the benefit of Korean Patent Application No. 10-2019-0079536, filed on Jul. 2, 2019. The entire disclosures of the above applications are incorporated herein by reference in their entirety.

TECHNICAL FIELD

The present invention relates to a hybrid-type artificial limb device and a control method therefor, and more specifically to a femoral artificial limb device including a knee joint member enabling flexion of the knee and a method for controlling the device.

BACKGROUND ART

For a person with a prosthetic leg such as the femoral artificial limb, it is a basic wish to take natural steps like a normal person. In particular, it is very difficult for a person with a prosthetic leg to climb stairs by alternately stepping on the left and right feet or to walk on a slope with a certain inclination. In this case, a firm knee braking function capable of preventing a fail, that is, a flexion control performance is the most important function required for wearing a prosthetic leg. In addition, if an active joint torque in an extension direction can be provided to lift the body weight upward, it can be of great help in overcoming stairs or upward slopes.

As can be seen from FIG. 1, the gait section of a person's walking is divided into a stance phase where a foot touches the ground and moves, and a swing phase section where a foot moves away from the ground. When a normal person walks, the knee goes through 2 flexions and 1 extension in the stance phase section, and 1 flexion and 1 extension in the swing phase section.

Referring to FIG. 1, in most cases of disabled persons with amputation, they pass the stance phase at a flat knee angle without stance flexion during walking, and then go directly to the swing phase section. Since the stance phase on the side of wearing an artificial limb is unstable, it has a relatively short stance phase. This is a fundamental cause of disabled persons with amputation who wear an artificial limb walking asymmetrically.

Artificial limb devices for disabled persons with amputation, which have been developed to allow disabled persons with amputation to walk more naturally, are largely divided into passive-type artificial limbs, variable damping-type artificial limbs and active-type artificial limbs.

The passive-type artificial limbs use a hydraulic cylinder to provide only passive forces by the hydraulic cylinder when a disabled person with amputation is walking, and these are made only with mechanical elements, and the joint resistance values can be adjusted manually before walking, but during walking, it has only one preset joint resistance. Since such a passive-type artificial limb is manufactured only with mechanical elements, there is no problem such as battery discharge, and it has strengths in terms of reliability and durability of the artificial limb. However, since a passive artificial limb has only one knee resistance which is set manually during walking, its ability to adapt to walking speed is relatively low, and it consumes 60% or more energy than healthy people due to asymmetric walking patterns and hip hiking problems, and it has a disadvantage in that the walking speed is slower than that of a normal person.

The variable damping-type artificial limbs are artificial limbs that are constituted with the goal of adjusting the hydraulic pressure and damping values of an MR/ER damper in real time to adjust the knee joint resistance in real time to be suitable for the walking situation. Currently, the most commonly used variable damping-type artificial limb, to which a hydraulic cylinder is applied, has advantages of improving knee stability and adaptability to the difference in walking speeds, compared to the passive-type artificial limb, by controlling the hydraulic pressure inside the hydraulic cylinder through a hydraulic nozzle in real time. However, since the variable damping-type artificial limb also uses a hydraulic cylinder, which is a passive mechanical element, it cannot provide an active driving force. Therefore, there is a disadvantage in that it cannot provide all of the power necessary for daily life, because it cannot be applied in situations where force in an extension direction must be applied to the knee, such as walking or running on stairs or slopes.

The active-type artificial limbs are artificial limbs using a driving motor that can provide a knee torque in an extension direction required for walking. The active-type artificial limb can provide an adequate force even when a large amount of power is required, such as on a slope or fast walking, and it can restore most activities of daily life. However, since the active-type artificial limb continuously uses the driving motor to move the artificial limb with power during both the stance phase and swing phase sections, it is difficult to be used continuously for a long period of time because of the large consumption of the battery. Further, there are disadvantages in that in order to generate a large force, the size of the power unit increases, the control of the system becomes complicated, and the weight is large.

Therefore, by supplementing the disadvantages of the conventional passive-type artificial limb, variable damping-type artificial limb and active-type artificial limb described above, it is necessary to develop an artificial limb device that can provide adequate power when the disabled person with amputation needs more than a certain amount of power when moving not only on flat ground but also on stairs or ramps, and that can be used for a long period of time due to low energy loss.

DISCLOSURE

Technical Problem

An exemplary embodiment of the present invention is directed to providing an artificial limb device capable of providing a torque in an appropriate extension direction required for movement when an artificial limb wearer needs a large force when moving, such as stairs or ramps, as well as on flat ground.

An exemplary embodiment of the present invention is directed to providing an artificial limb device that can be used for a long period of time with low energy loss.

An exemplary embodiment of the present invention is directed to providing a hybrid-type artificial limb device capable of appropriately providing the required force to an artificial limb wearer while reducing energy loss by combining the advantages of a passive-type artificial limb and an active-type artificial limb.

Technical Solution

According to an aspect of the present invention, provided is a hybrid-type artificial limb device, including a joint upper side connection member positioned at the upper side of a knee, a knee joint member connected to the joint upper side connection member, and a frame coupled to the knee joint member to be able to perform a pivot rotation, and forming a femoral part, and further including a passive driving module which includes a hydraulic cylinder connected to the knee joint member, so as to transfer passive power to the knee joint member, and an active driving module which is coupled to the knee joint member so as to transfer active power to the knee joint member, wherein when the frame performs a pivot rotation about the knee joint member, the passive power from the passive driving module and the active power from the active driving module may be selectively or simultaneously provided to the knee joint member.

In this case, one end of the hydraulic cylinder in an extension direction may be operatively coupled to the knee joint member at a location around the knee joint member, and the other end of the hydraulic cylinder in an extension direction may be connected to the end side in a direction away from the knee joint member of the frame.

In this case, the active driving module may include a first pulley coupled to the knee joint member; a second pulley positioned at one end of the frame in a direction away from the knee joint member; a driving cable operatively connecting the first pulley and the second pulley; and a driving motor for actively driving the driving cable.

In this case, the first pulley may be arranged concentrically with the rotation axis of the knee joint member.

The first pulley may be formed integrally with the knee joint member.

The first pulley may be operatively coupled to the knee joint member so as to be simultaneously rotatable.

The hydraulic cylinder of the passive driving module may be disposed parallel to a plane on which the driving cable of the active driving module operates.

In this case, the hybrid-type artificial limb device may further include a clutch module connected between the cable and the driving motor so as to selectively transmit power of the driving motor to the driving cable.

In this case, when the power of the driving motor is connected to the cable by the clutch module in a transferable state, the clutch module moves together with the cable.

In this case, the frame may be provided with a guide member for guiding the movement of the clutch module when the clutch module moves together with the cable.

In this case, when the active driving module is connected to the cable by the clutch module in a state where the power of the driving motor is transferable, the driving motor moves the guide member such that the clutch module connected to the guide member and the cable are formed to move together, and the pivot rotation of the frame about the knee joint member may be made according to the movement of the cable.

According to another aspect of the present invention, provided is a method for controlling a hybrid-type artificial limb device, and the hybrid-type artificial limb device includes a joint upper side connection member positioned at the upper side of a knee, a knee joint member connected to the joint upper side connection member, and a frame coupled to the knee joint member to be able to perform a pivot rotation, and forming a femoral part, and further includes a passive driving module and an active driving module connected to the knee joint member, wherein under a first walking condition of a user who is equipped with the artificial limb device, the user walks using the passive driving module that transmits passive power to the knee joint member, and wherein under a second walking condition of a user who is equipped with the artificial limb device, the user walks using the active driving module that is connected to the knee joint member.

In this case, the first walking condition of the user is to walk on flat ground with an inclination angle which is less than a predetermined angle.

In this case, under the first walking condition, the active driving module may be formed to cut off power transmission to the knee joint member, when walking using the passive driving module.

In this case, the second walking condition of the user is to walk on an incline with an inclination angle which is greater than or equal to a predetermined angle, run or climb stairs.

In this case, under the second walking condition of the user, the active driving module may be mechanically controlled such that power is transmitted to the knee joint member only when walking using the active driving module.

In this case, a condition in which the active driving module operates when walking on an incline in the second walking condition of the user is when a knee angular velocity changes from positive to negative and the angular velocity instantly becomes 0, and a condition in which the active driving module is released when walking on an incline in the second walking condition of the user is when a knee angular velocity changes from negative to positive and the angular velocity instantly becomes 0.

In this case, a condition in which the active driving module operates when climbing stairs in the second walking condition of the user is when a knee angular velocity changes from positive to negative and the angular velocity instantly becomes 0, and wherein a condition in which the active driving module is released when climbing stairs in the second walking condition of the user is when a knee angular velocity changes from negative to positive and the angular velocity instantly becomes 0.

In this case, the active driving module and the passive driving module may operate together under the second walking condition.

In this case, the active driving module nay operate within a stance phase range of the user under the second walking condition of the user.

[Advantageous Effects]

The hybrid-type artificial limb device according to an exemplary embodiment of the present invention can appropriately provide an artificial limb wearer with the force required for daily life by using a passive driving module to walk during normal walking on flat ground, and using an active driving module to move during moving which requires a large amount of force, such as walking on a slope or climbing stairs.

In the case of using a passive driving module, the hybrid-type artificial limb device according to an exemplary embodiment of the present invention has an advantage that it can be used for a long period of time due to low energy loss, because it does not use an active driving module. In particular, in the case of walking on flat ground, walking on a descending slope and walking on stairs, the energy saving effect is great because it is possible to walk using only the passive driving module.

In addition, the hybrid-type artificial limb device according to an exemplary embodiment of the present invention can limit unnecessary power use for operating by having a clutch structure in which the driving module may be mechanically disconnected from the knee joint when the active driving module is not used.

DESCRIPTION OF DRAWINGS

FIG. 9 is a graph where the x-axis shows the knee angular velocity (RPM), and the y-axis shows the averaged torque (a value obtained by dividing the knee torque by the body weight of a disabled person with amputation), and FIG. 10 is a graph where the x-axis shows time and the y-axis shows the knee angle. In FIG. 9, in the case of the knee angular velocity of the x-axis, a positive value indicates a bending direction speed, and a negative value indicates an extension direction speed, and in the case of the averaged torque of the y-axis, a positive value indicates an extension direction torque, and a negative value indicates a flexion direction torque. In FIG. 10, the x-axis represents one cycle time of the human gait cycle, and the y-axis represents the relative knee joint angle, and a positive value represents the relative flexion angle of the shin compared to the femoral part.

FIG. 13 is a graph where the x-axis represents the knee angular velocity and the y-axis represents the averaged torque, and FIG. 14 is a graph where the x-axis represents time and the y-axis represents the knee angle.

MODES OF THE INVENTION

Figure 1:
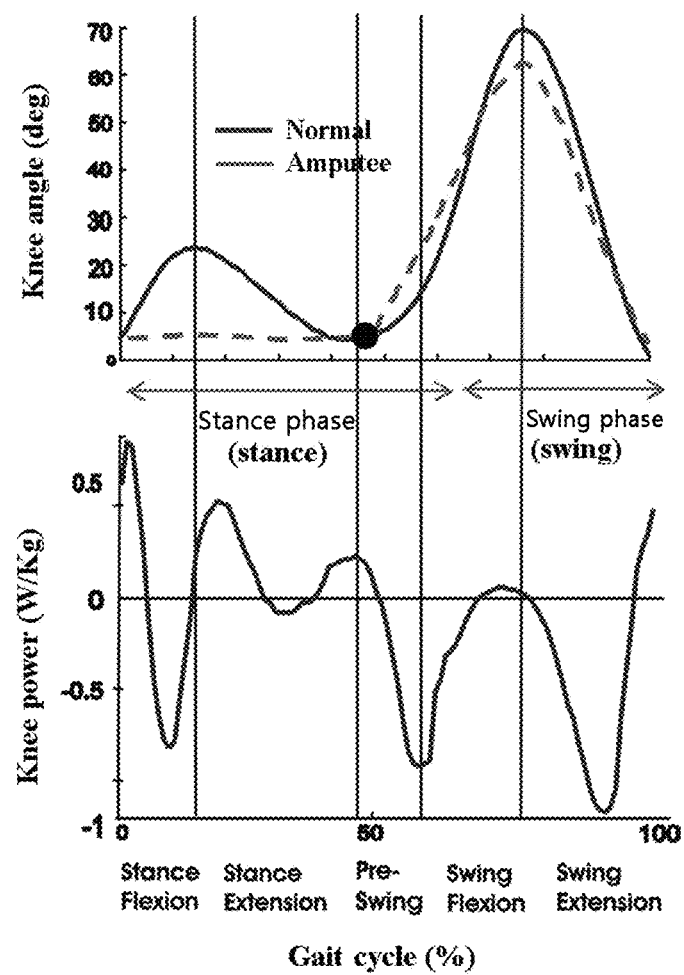
FIG. 1 is a diagram showing the knee angle and knee power in stance and swing phases when a person walks. The solid line represents the knee angle of a normal person, and the dotted line represents the knee angle of a disabled person with amputation during walking.

Hereinafter, exemplary embodiments of the present invention will be described in detail with reference to the accompanying drawings such that those of ordinary skill in the art to which the present invention pertains may easily practice the present invention. The present invention may be implemented in various different forms, and is not limited to the exemplary embodiments described herein. In the drawings, parts irrelevant to the description are omitted in order to clearly describe the present invention, and the same reference numerals are assigned to the same or similar components throughout the specification.

Figure 2:
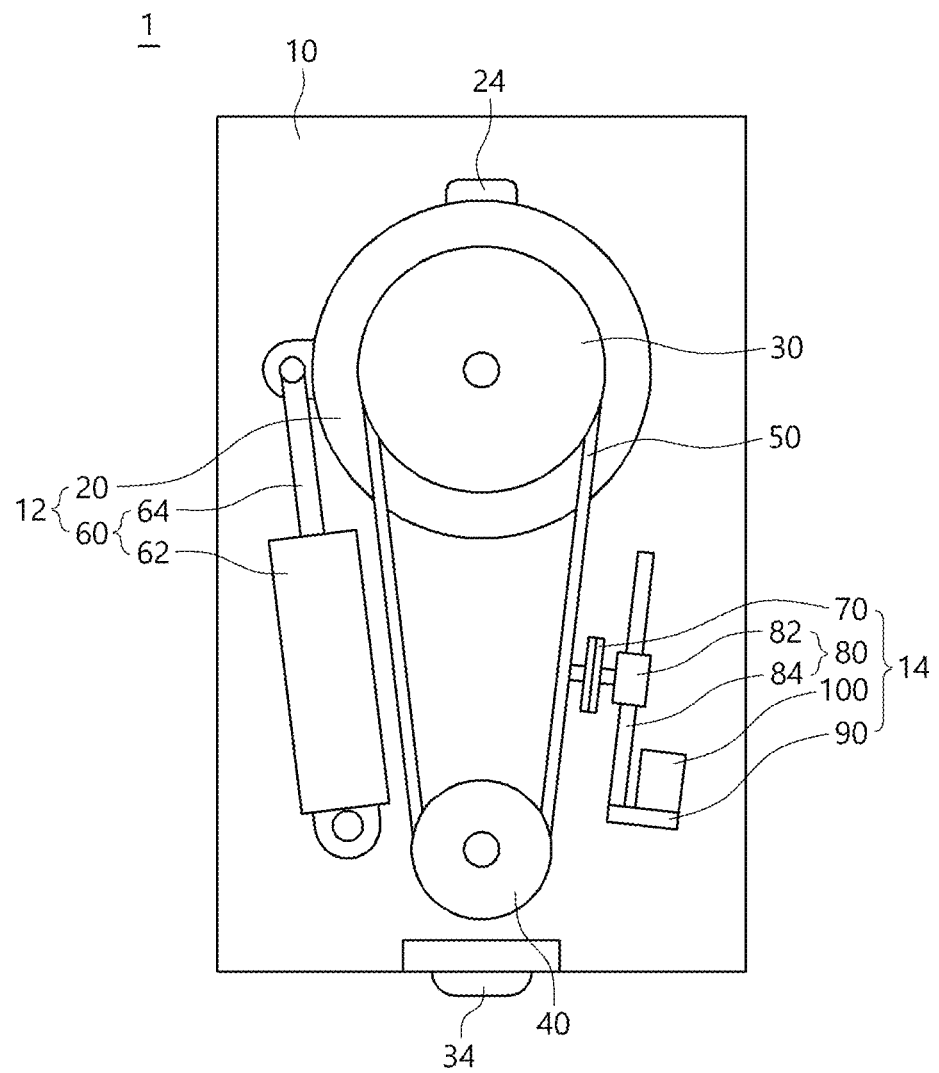
FIG. 2 is a schematic configuration diagram of a hybrid artificial limb device according to an exemplary embodiment of the present invention.
Figure 3:
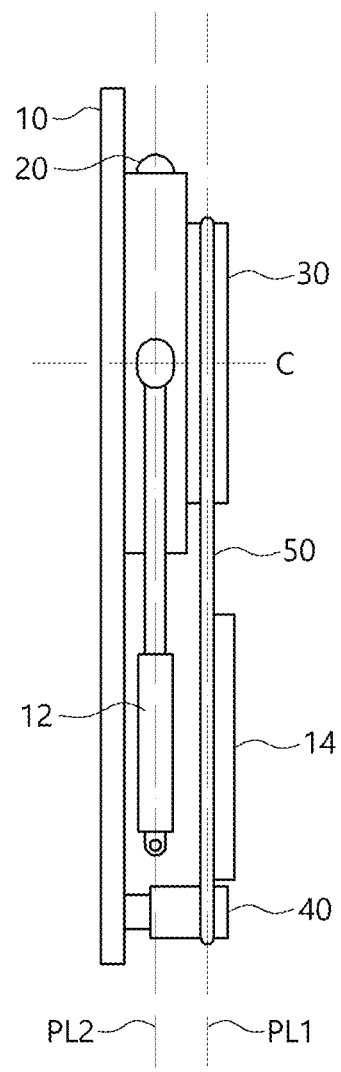
FIG. 3 is a diagram as viewed from the side of FIG. 2.
Figure 4A:
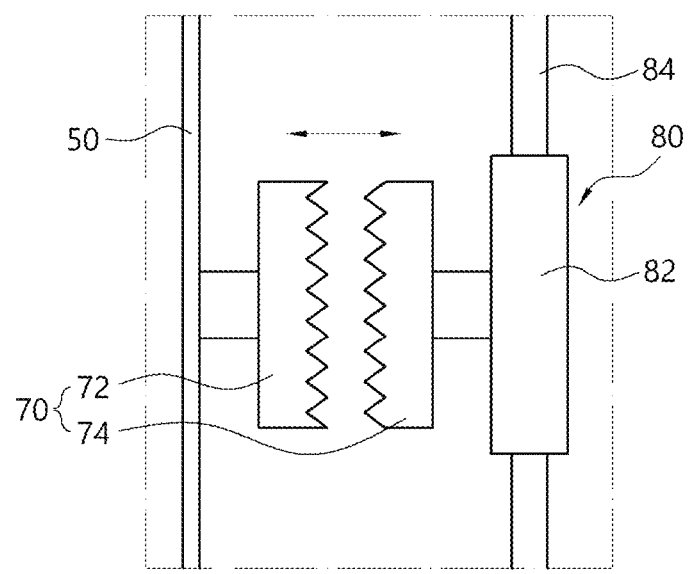
FIG. 4a is an example of the clutch module gear part of the hybrid artificial limb device according to an exemplary embodiment of the present invention.
Figure 4B:
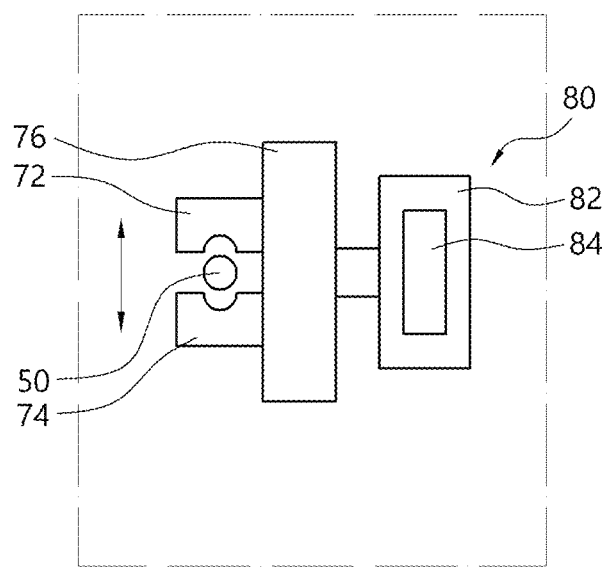
FIG. 4b is another example of the clutch module.
Figure 5:
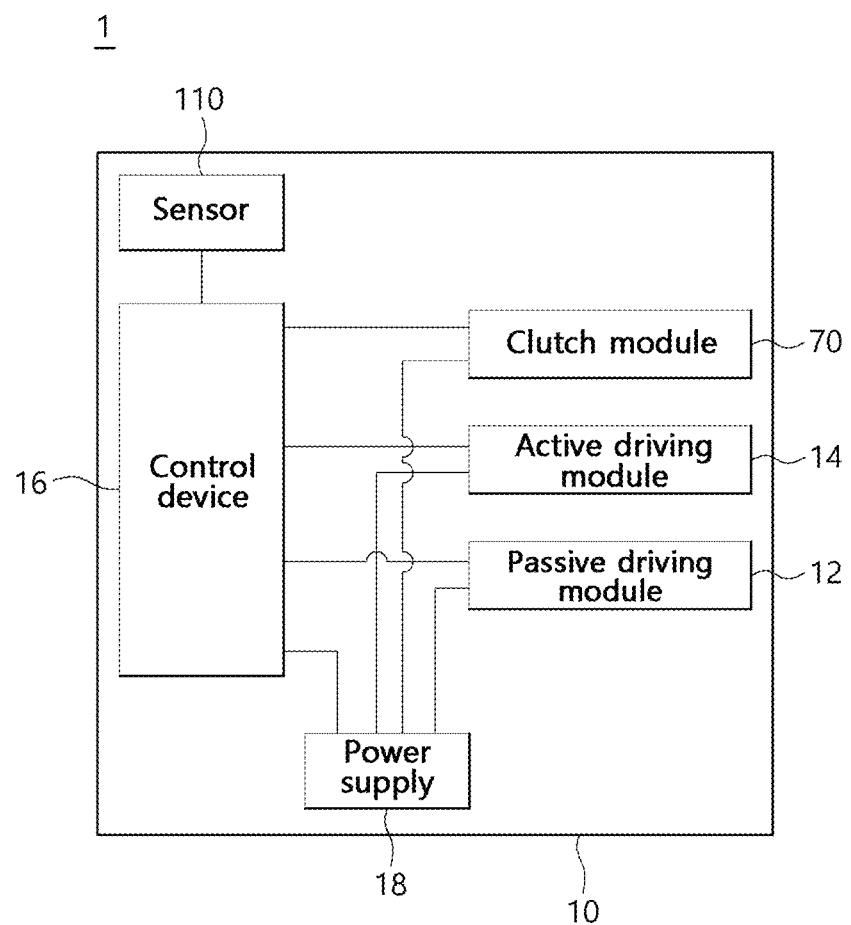
FIG. 5 is a system configuration diagram of the hybrid artificial limb device according to an exemplary embodiment of the present invention.

FIG. 2 is a schematic configuration diagram of a hybrid artificial limb device according to an exemplary embodiment of the present invention. FIG. 3 is a diagram as viewed from the side of FIG. 2. FIG. 4a is an example of the clutch module gear part of the hybrid artificial limb device according to an exemplary embodiment of the present invention, and FIG. 4b is another example of the clutch module. FIG. 5 is a system configuration diagram of the hybrid artificial limb device according to an exemplary embodiment of the present invention.

Referring to FIGS. 2 and 5, the hybrid artificial limb device 1 according to an exemplary embodiment of the present invention may include a frame 10, a passive driving module 12 and an active driving module 14.

The frame 10 forms an outer housing or a skeleton of the hybrid-type artificial limb 1, on which components constituting the artificial limb device are mounted, and may be formed, for example, in a plate shape having a predetermined form. As seen in FIG. 2, the frame 10 may be formed in a shape that extends in the vertical direction, and in the present exemplary embodiment, it is illustrated in the shape of a plate in a square shape for helping the understanding, but the shape of the frame is not limited thereto.

When the frame 10 forms at least a part of the outer housing of the artificial limb device, components constituting the artificial limb device are embedded inside the frame 10 to be protected from the outside. Meanwhile, when the frame 10 forms the skeleton of the artificial limb device, a separate housing for protecting the frame 10 and the components may be provided outside the frame 10 while the components (e.g., a hydraulic cylinder, a cable, etc. described below) constituting the artificial limb device are installed on the frame 10. In this case, the separate housing may be formed to have a curved shape similar to the lower leg shape of the human body.

Meanwhile, in the present exemplary embodiment, a knee joint member 20 is provided on the upper side of the frame 10. The knee joint member 20 is a part that forms a knee joint when the hybrid-type artificial limb device of the present invention is mounted on an artificial limb wearer. Referring to FIG. 2, the knee joint member 20 according to an exemplary embodiment of the present invention is made in, for example, a cylindrical shape and is formed to have a central axis of rotation at the center. In this case, in the present exemplary embodiment, the knee joint member 20 is illustrated as having a cylindrical shape, but this is to facilitate the understanding of the components, and the outer peripheral surface of the knee joint member 20 may be formed to have a shape other than a cylindrical shape.

A joint upper connection member 24 may be provided on the upper side of the knee joint member 20 to be coupled to a structure such as a socket fixed to the lower side of the femoral part of the artificial limb wearer. The joint upper connection member 24 may be formed in the form of a projection protruding from the knee joint member 20, but the shape of the joint upper connection member 24 may be made in various ways depending on the shape of a socket or a femoral side coupling part of the artificial limb wearer, to which the joint upper connection member 24 is coupled. The upper joint connection member 24 may be directly installed on the knee joint member 20 or may be indirectly connected by a separate connection structure. According to an exemplary embodiment of the present invention, while the joint upper connection member 24 is connected to the socket of the artificial limb wearer, the knee joint member 20 serves as a knee joint, and by pivoting the frame 10 with respect to the knee joint member 20, a bending action of the knee may be achieved.

Meanwhile, as seen in FIG. 2, an ankle joint connection member 34 may be formed in the lower portion of the frame 10 such that the ankle joint is connected to the frame 10.

According to an exemplary embodiment of the present invention, in order to add a rotational force to the knee joint member 20, a passive driving module 12 and an active driving module 14 are installed in the frame 10.

The passive driving module 12 may include a hydraulic cylinder 60 and a knee joint member 20 installed on the frame 10.

The hydraulic cylinder 60 is composed of a body portion 62 having an inner space through which fluid can flow in and out and a piston portion 64 that can reciprocate and move in an outward direction as the fluid flows in and out of the body portion 62.

The hydraulic cylinder 60 is disposed in the vertical direction as seen in FIG. 2 and in an extension direction of the frame 10, and one end in an extension direction located on the upper side of the frame 10, that is, the end in an extension direction of the piston portion 64 is rotatably coupled to the knee joint member 20 at a location on the outer peripheral side of the knee joint member 20. In addition, the other end of the hydraulic cylinder 60 in an extension direction, that is, the end of the body portion 62 is rotatably coupled to the lower side of the frame 10.

In this way, since one end of both ends of the hydraulic cylinder 60 is rotatably coupled to the knee joint member 20 and the other end is rotatably coupled to the lower side of the frame 10, the frame 10 may pivot and rotate relative to the knee joint member 20, when the piston portion 64 of the hydraulic cylinder 60 extends or contracts. In this case, the attachment position of the hydraulic cylinder and the movement range of the piston are set based on the knee angle rotation range when the human walks.

In an exemplary embodiment of the present invention, the hydraulic cylinder 60 is formed to provide a passive force at a constant pressure to the knee joint in a known manner, or is made of a known variable damping type to be formed so as to control the size of the hydraulic pressure inside the hydraulic cylinder 60, and when the passive module is used, the damping force may be appropriately adjusted in consideration of the gait cycle.

The hydraulic cylinder 60 may have a fluid control valve and the like installed inside or outside the body portion 62 to control hydraulic pressure, and an additional configuration for supplying or discharging fluid into the hydraulic cylinder 60 may be additionally provided. As for the detailed configuration of the hydraulic cylinder for controlling such a passive drive, a known configuration may be applied, and a detailed description thereof will be omitted.

Meanwhile, the active driving module 14 of the hybrid-type artificial limb device 1 according to an exemplary embodiment of the present invention is for transmitting active power to the knee joint member 20, and may include a first pulley 30, a second pulley 40, a driving cable 50 and a driving motor 100.

In this case, the first pulley 30 is disposed concentrically with the rotation axis C of the knee joint member 20 and is formed to be rotatable at the same time as the knee joint member 20. For example, the first pulley 30 may be integrally formed with the knee joint member 20 or may be formed as a separate member.

Referring to FIG. 2, the first pulley 30 may be formed in a cylindrical shape having a diameter smaller than that of the knee joint member 20, but this is only illustrative to facilitate the understanding of the configuration, and the size of the first pulley 30 is not limited thereto.

Further, in the present exemplary embodiment, although the first pulley 30 is exemplified to be disposed concentrically with the rotation axis of the knee joint member 20, when the rotation axis of the first pulley 30 is operatively connected to the knee joint member 20 by a separate gear, an intermediate connecting member (e.g., a link member) or the like, it may also be possible that the rotation axis of the first pulley 30 is not arranged concentrically with the rotation axis of the knee joint member 20.

The second pulley 40 is rotatably installed on the lower side of the frame 10 as seen in FIG. 2. The second pulley 40 may be formed of a cylindrical member having a diameter smaller than or equal to that of the first pulley 30.

A driving cable 50 is wound around the first pulley 30 and the second pulley 40 such that the first pulley 30 and the second pulley 40 may be rotatable at the same time. Since the hybrid-type artificial limb device 1 according to an exemplary embodiment of the present invention allows the first pulley 30 to rotate by moving the driving cable 50, and allows the knee joint member 20 to rotate according to the rotation of the first pulley 30, it is configured to apply an active force to the knee joint member 20.

In this case, referring to FIG. 3, in the hybrid-type artificial limb device 1 according to an exemplary embodiment of the present invention, a second plane PL2 on which the hydraulic cylinder 60 operates is disposed to be parallel to a first plane PL1 on which the driving cable 50 wound around the first pulley 30 and the second pulley 40 operates.

More specifically, in the hybrid-type artificial limb device 1 according to an exemplary embodiment of the present invention, the driving cable 50 for providing active power to the first pulley 30 operates on the first plane PL1, and the hydraulic cylinder 60 providing passive power to the knee joint member 20 operates on the second plane PL2.

In this case, since the first pulley 30 and the knee joint member 20 are formed to rotate at the same time and the first plane PL1 and the second plane PL2 are arranged parallel to each other, the hybrid artificial limb device 1 according to an exemplary embodiment of the present invention may compactly arrange the passive driving module 12 and the active driving module 14 in a space that is not spatially large.

A driving motor 100 is provided on one side of the frame 10 in order to move the driving cable 50 wound around the first pulley 30 and the second pulley 40.

According to an exemplary embodiment of the present invention, a power transmission member 90, a guide member 80 and a clutch module 70 are provided to transmit the driving force of the driving motor 100 to the driving cable 50.

The power transmission member 90 is a component which is coupled to the driving motor 100 for transmitting the power of the driving motor 100 toward the driving cable 50. For example, the power transmission member 90 may be a pulley, a gear or other known power transmission member.

The guide member 80 is a component which is connected to the power transmission member 90 connected to the driving motor 100 for guiding the movement of the driving cable 50. As the guide member 80, for example, a known guide member such as a linear guide module 82 capable of moving on a guide rail 84 or a ball nut capable of linearly moving along a ball screw may be used.

According to an exemplary embodiment of the present invention, a linear guide module or a ball nut of a ball screw that can be moved linearly from the guide member 80 is directly or indirectly connected to the driving cable 50 to move together with the driving cable 50.

In this case, while the driving cable 50 is wound around the first pulley 30 and the second pulley 40, the moving distance of the driving cable 50 may be formed to be equal to the moving distance of the guide member 80. The rotational direction, rotational speed and angle of the first pulley 30 are changed according to the distance, speed and direction in which the driving cable 50 moves, and accordingly, the bending angle and speed of the knee joint member 20 operatively coupled to the first pulley 30 are changed.

Although the guide member 80 may be directly and fixedly connected to the cable, the hybrid-type artificial limb device 1 according to an exemplary embodiment of the present invention is provided with a clutch module 70 and formed so as to selectively transfer the power of the driving motor 100 to the driving cable 50.

More specifically, referring to FIGS. 4A and 4B, the clutch module 70 may be made of, for example, a first portion 72 coupled toward the driving cable 50 and a second portion 74 coupled to the guide member 80.

In this case, the first portion 72 and the second portion 74 may be formed to be mutually fastened or separated. In this way, in order to fasten or separate the first portion 72 and the second portion 74, the first portion 72 and the second portion 74 may be formed in a mutually movable coupling structure, and a separate driving portion may be provided for moving any one of the first portion 72 and the second portion 74 relatively to the other one.

For example, one side of the first portion 72 and the opposite side of the second portion 74 may have a structure that can be interlocked with each other as illustrated in FIG. 4a, and when both sides are in contact with each other and interlocked, the first portion 72 and the second portion 74 are formed to move at the same time, and such a case may be defined as a clutch 'on' state, in which the power of the driving motor 100 may be transmitted to the driving cable 50.

Conversely, when one side of the first portion 72 and the opposite side of the second portion 74 are spaced to be separated from each other, the first portion 72 and the second portion 74 are mechanically separated from each other and it is impossible to move at the same time, and such a case may be defined as a clutch 'off' state, in which the power of the driving motor 100 may not be transmitted to the driving cable 50.

In this case, in the first portion 72 and the second portion 74 as illustrated in FIGS. 2 and 4a, although the first portion 72 may be directly coupled to the driving cable 50 and the second portion 74 may have a structure coupled to the guide member 80, the structures of the first portion 72 and the second portion 74 are not limited thereto.

As another example, as illustrated in FIG. 4b, the first portion 72 and the second portion 74 are both coupled to the guide member, but while the first portion 72 and the second portion 74 are made in a clamp-type structure or a guide structure in the clutch 'on' state, the first portion 72 and the second portion 74 are fixed or coupled in contact with the driving cable 50 while these are close to each other, and the first portion 72 and the second portion 74 are formed so as to be movable together with the driving cable 50 and formed such that power may be transmitted.

In addition, in the clutch 'off' state, at least one of the first portion 72 and the second portion 74 moves away from the driving cable 50 and is disengaged, and thus, the first portion 72 and the second portion 74 are formed such that these may not move together with the driving cable 50, and thus power is not transmitted. In order to move the first portion 72 and the second portion 74 closer to each other or away from each other, a guide 76 which operatively supports the first portion 72 and the second portion 74 may be provided additionally. When the first portion 72 and the second portion 74 have a clamp-type structure, these may be formed in a structure in which these are coupled to each other so as to be pivotable.

In this case, the structure of mutually coupling the first portion 72 and the second portion 74 so as to move simultaneously with the driving cable 50 may be a mechanical coupling structure or an electrical coupling structure as described above.

Meanwhile, referring to FIG. 5, the hybrid-type artificial limb device 1 according to an exemplary embodiment of the present invention may include a sensor 110 and a controller 16 so as to operate the passive driving module 12, the active driving module 14 and the clutch module 70 described above.

The sensor 110 may include various sensors for detecting a start time point and an end time point at which the passive driving module 12 and the active driving module 14 should operate, respectively. Such sensors may include, for example, a sensor for measuring the angle and rotational speed of the knee, a sensor for detecting the moving speed of the artificial limb wearer, a sensor for measuring the height of the knee, a sensor for measuring the force acting on the knee and the like, but the type of sensors is not limited thereto.

Meanwhile, a controller 16 may be provided to operate at least one of the passive driving module 12, the active driving module 14 and the clutch module 70 using the sensing value measured by the sensor 110. The controller 16 may be implemented as a data processing device in the form of an integrated circuit installed on a known PCB substrate, and data may be transmitted and received by wired or wireless communication with the sensor 110, the passive driving module 12, the active driving module 14 and the clutch module 70.

Figure 6:
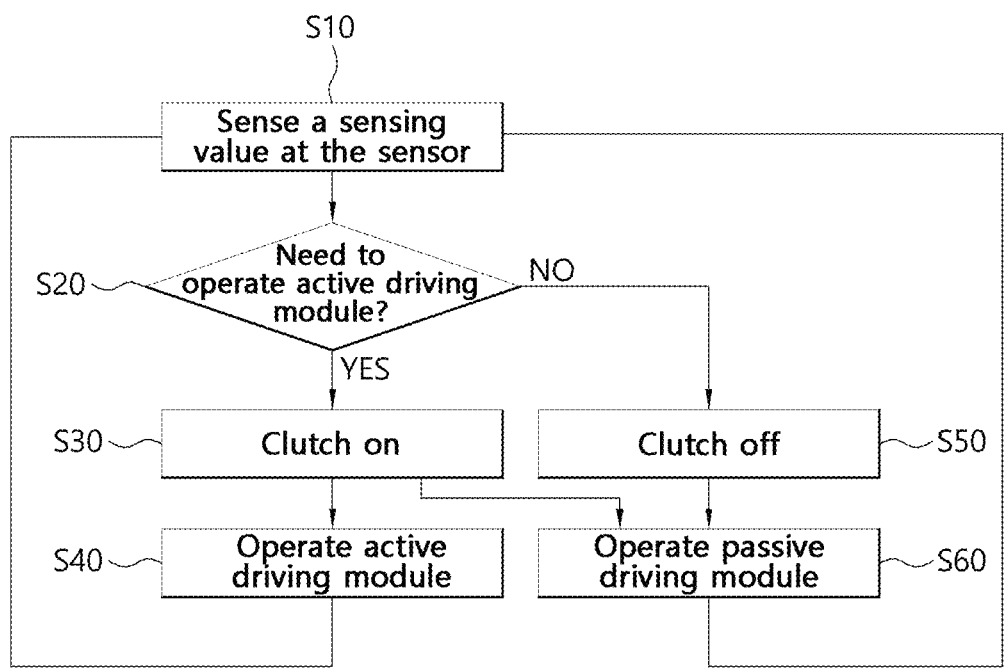
FIG. 6 is a flow chart illustrating the method for operating a hybrid artificial limb device according to an exemplary embodiment of the present invention.
Figure 7:
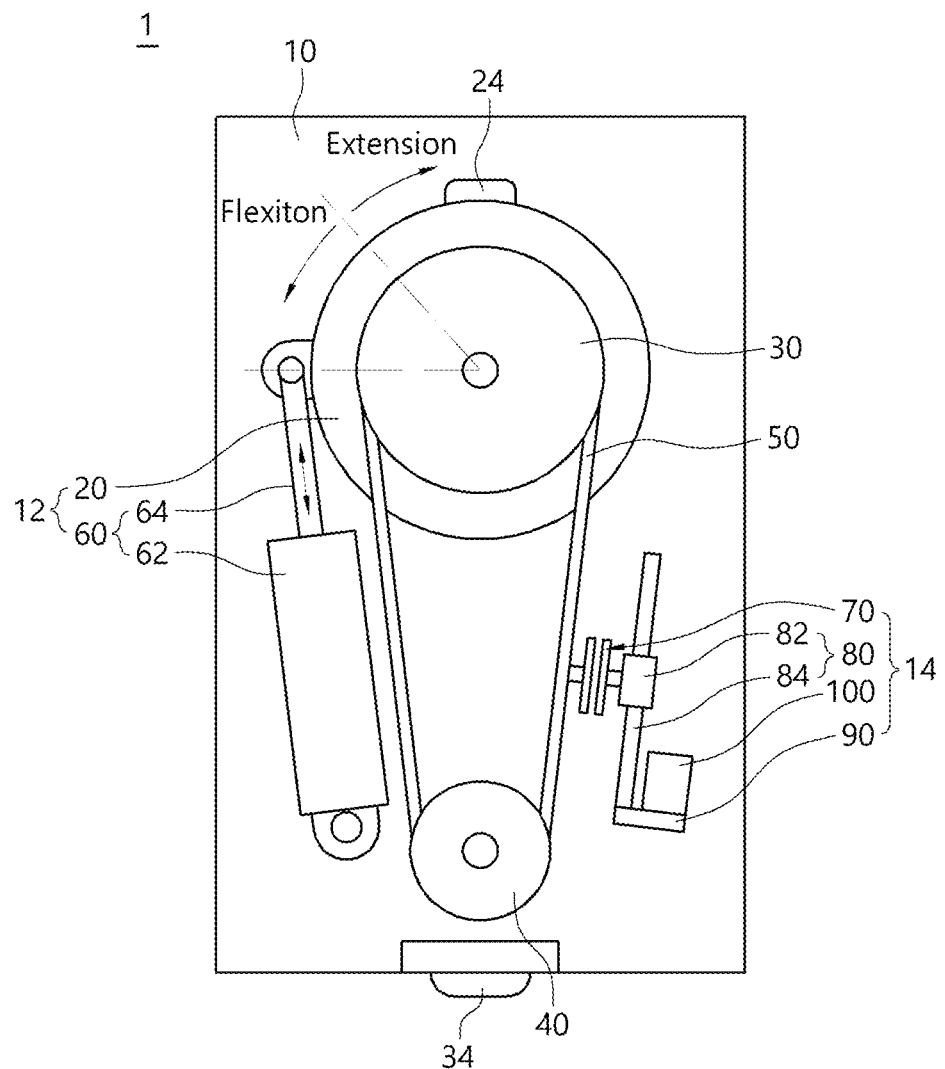
FIG. 7 is a diagram showing a state where the hybrid artificial limb device is operated using a passive driving module in the hybrid artificial limb device according to an exemplary embodiment of the present invention.
Figure 8:
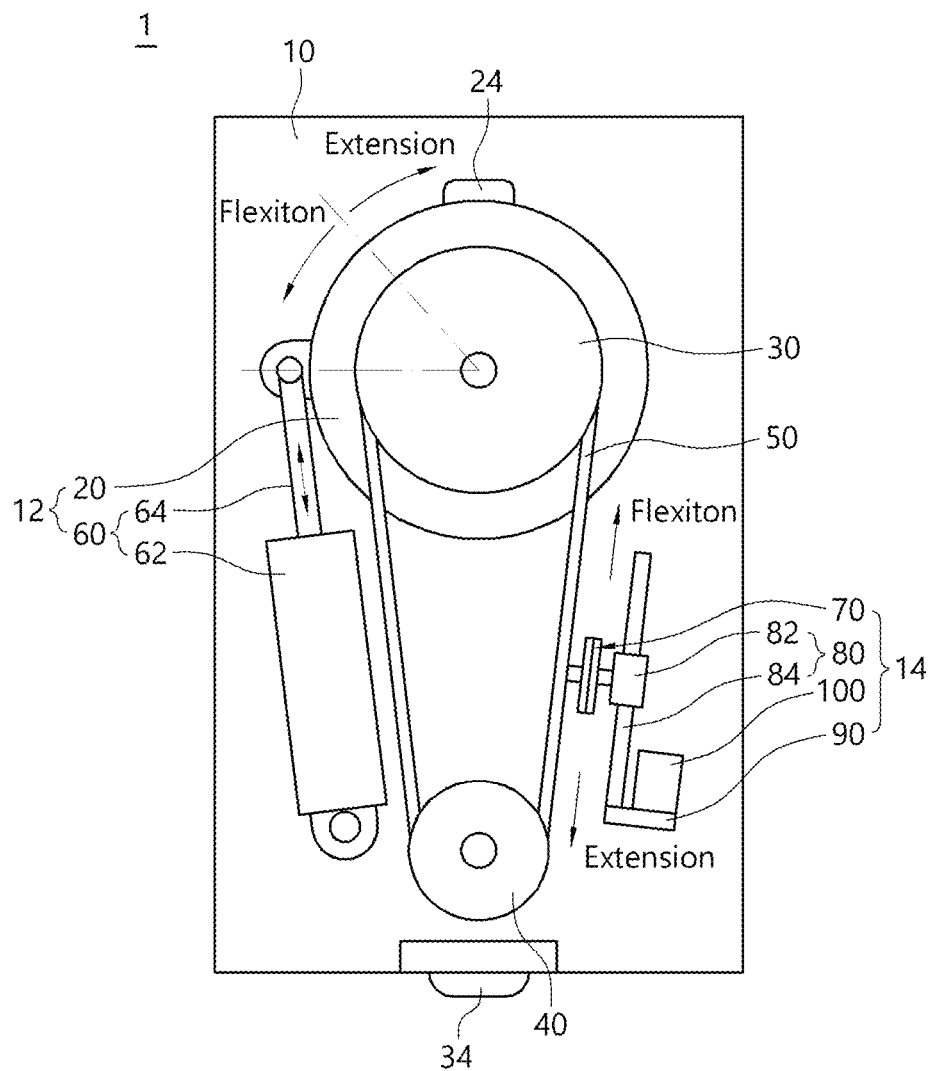
FIG. 8 is a diagram showing a state where the hybrid artificial limb device is operated using an active driving module in the hybrid artificial limb device according to an exemplary embodiment of the present invention.

FIG. 6 is a flow chart illustrating the method for operating a hybrid artificial limb device according to an exemplary embodiment of the present invention. FIG. 7 is a diagram showing a state where the hybrid artificial limb device is operated using a passive driving module in the hybrid artificial limb device according to an exemplary embodiment of the present invention. FIG. 8 is a diagram showing a state where the hybrid artificial limb device is operated using an active driving module in the hybrid artificial limb device according to an exemplary embodiment of the present invention.

Referring to FIG. 6, while a user equipped with the hybrid artificial limb device 1 according to an exemplary embodiment of the present invention is walking, the sensor 110 of the artificial limb device measures a sensing value S10. In this case, according to the measured sensing value, the controller 16 determines whether the active driving module 14 should be operated or whether the active driving module 14 should not be operated S20.

When the active driving module 14 is not required, for example, when a large force is not required, such as walking on flat ground, the controller 16 turns off the clutch module 70 S50, and it allows walking to be performed only by the passive driving module S60. FIG. 7 illustrates a state in which the operation is performed only by the passive driving module 12 while the clutch module 70 is turned off.

Referring to FIG. 7, the hydraulic cylinder 60 operates in a flexion state when the artificial limb wearer walks, and as seen in FIG. 7, the knee joint member 20 rotates relatively about the femoral part in a counterclockwise direction, and in an extension state, the hydraulic cylinder is extended, and the knee joint member rotates relatively about the femoral part in a clockwise direction as seen in FIG. 7.

In this case, the hydraulic cylinder 60 imparts a passive force to the knee joint member 20 such that the artificial limb wearer may walk with minimum power or without using power while walking.

In the clutch-off state while the passive driving module 12 is operating, the driving cable 50 simply remains hung on the first pulley 30 and the second pulley 40 and is passively rotated while being wound between the first pulley 30 and the second pulley 40 according to the operation of the hydraulic cylinder 60.

While the passive driving module 12 is operating, the sensor 110 continuously measures the sensing value, and it is determined whether the artificial limb wearer should continue to walk using only the passive driving module 12 or whether to operate the passive driving module while walking.

When the controller 16 determines that active power is required while the artificial limb wearer is walking, for example, when it is determined that it is a case of walking on a slope, running or performing an operation of climbing stairs, the controller 16 turns on the clutch module 70 S30, and the active driving module 14 is operated S40. FIG. 8 illustrates a state in which the active driving module 14 is operated as described above.

Referring to FIG. 8, when the clutch module is 'on', the driving force of the driving motor 100 is transmitted to the driving cable 50 through the guide member 80, and when the driving motor 100 is operated, the clutch module 70 and the driving cable 50 are moved together with the guide member 80. In this case, only the force transmission in an extension direction is possible due to the structure of the gear, and the force transmission in a flexion direction does not occur.

Referring to FIG. 8, when the artificial limb wearer walks, in a flexion state, the driving cable 50 moves upward as seen in FIG. 8 to move the first pulley 30 in a counterclockwise direction, and likewise, as the first pulley 30 moves, the knee joint member 20 moves by receiving a force that moves in a counterclockwise direction relative to the femoral part. In this case, when large flexion movements occur repeatedly for a long period of time, the gear teeth are separated from the clutch module to reduce rotational inertia, and in this case, the driving motor is completely separated from the knee module to reduce the rotational load, and thus, it is possible to minimize energy consumption.

Further, when the artificial limb wearer walks, in an extension state, the driving cable 50 moves downward as seen in FIG. 8 to move the first pulley 30 in a clockwise direction, and likewise, as the first pulley 30 moves, the knee joint member 20 moves by receiving a force that moves in a clockwise direction relative to the femoral part.

In this way, while the active driving module 14 adds active power to the knee joint member 20 through the first pulley 30, the hydraulic cylinder 60, which has applied the passive driving force, acts as a reaction force of the active driving force to add a damping force to the rotational force of the knee joint member 20. Accordingly, when the active driving module 14 is operated, the active driving force and the damping force act on the knee joint member 20 together, thereby making the movement of the artificial limb wearer smoother.

Meanwhile, in the case where the active driving module 14 is to be operated, for example, when it is difficult to determine in a special situation that it is the corresponding situation only by the sensing of the sensor 110, despite the case that a specific force or more is required, such as when climbing stairs, it is also possible for the controller 16 to generate a specific trigger signal so as to recognize such a special situation. For example, the artificial limb wearer may repeat the motion of tapping the floor lightly with his heel twice in front of stairs. If the controller 16 detects that the operation of tapping the floor lightly with the heel is performed twice, the controller 16 recognizes that the artificial limb wearer is going to climb stairs, turns on the clutch module and then operates the active driving module. These trigger movements may be set in various ways.

While the active driving module 14 is operated, the sensor 110 continuously measures the sensing value, and while the sensor 110 measures the sensing value in this way, if it is recognized as a state where walking is possible only with the passive driving module 12, the operation of the active driving module 14 is stopped, the clutch module 70 is maintained in an off state, and then the passive driving module 12 may be operated.

In the method for controlling the hybrid-type artificial limb device 1 described above, it may be necessary to distinguish a time of walking by operating only the passive driving module 12 and a time of walking by operating the active driving module 14, and hereinafter, these will be described in more detail.

In a general walking situation in which a wearer of the hybrid artificial limb device 1 according to an exemplary embodiment of the present invention may walk using only the passive driving module 12, the active driving module 14 is maintained in a clutch-off state, and when a state where the driving module 14 is to be operated is detected, the clutch module 70 is turned on to operate the active driving module 14 and then the active driving module 14 is operated.

In this case, when the active driving module 14 applies active power to the knee joint member 20 through the first pulley 30, even in the process of the artificial limb wearer walking (when an active driving force must be added, such as climbing stairs, walking on an incline or running), it may be limited to a case where an active driving force is specifically required during the stance phase rather than the entire process of the stance and swing phases.

That is, in the method for controlling the hybrid-type artificial limb device 1 according to an exemplary embodiment of the present invention, even in a walking situation in which an active driving force is added through the active driving module 14, passive power is used to walk during the swing phase.

In this way, even in a situation in which the active driving power is provided by using the active driving module 14, since the active driving force is used only in some sections of the stance phase in a specific situation, the hybrid-type artificial limb device according to an exemplary embodiment of the present invention allows effective gait only with a small amount of energy, and it is possible to use the battery for a long period of time. Hereinafter, the situation and timing of using only the passive driving module 12 and the specific operating conditions and timing of the active driving module 14 under a specific situation of operating the active driving module 14 will be described in more detail.

In the method for controlling a hybrid-type artificial limb device according to an exemplary embodiment of the present invention, it may be defined that under a first walking condition, a passive driving module that transmits passive power is used to walk, and under a second walking condition, an active driving module that is coupled to the knee joint member is used to walk.

In this case, the first walking condition for walking using the passive driving module 12 may include walking on flat ground and walking in a downward slope, walking on a downward staircase, sitting while standing and the like. In this case, the inclination angle that determines whether the person is walking on flat ground may be set differently according to the walking ability and weight of a disabled person with amputation. Such walking on flat ground accounts for 60% or more of cases where the artificial limb wearer walks in daily life. Therefore, in such flat ground walking, since only the passive driving module 12 is used for walking, separate power is not used, and thus, energy of the battery consumed when walking on the flat ground may be reduced.

When walking using only the passive driving module 12 as described above, the clutch module 70 is maintained in an off state, and the active driving module 14 is formed such that power transmission to the knee joint member is cut off. Accordingly, in the first walking condition, the active module remains in a power-saving state in which it does not operate, and even if the active driving module 14 malfunctions, power is not transmitted by the clutch module 70, and thus, it is possible to minimize power consumption by the active driving module 14.

Meanwhile, the second walking condition for moving using the active driving module 14 may include walking on an upward slope at a predetermined angle of inclination, for example, 15 degrees or more, or walking fast or running at a predetermined speed or more, or climbing stairs. In this case, the angle of inclination, the running speed during running and the height of stairs when climbing the stairs may be set differently according to the magnitude of the force to be applied to the knee.

In this way, under the second walking condition in which the artificial limb wearer must move using the active driving module 14, when the active driving force is transmitted through the active driving module 14, the clutch is controlled to be turned on, and while the clutch is turned on, the active driving force is formed to transmit active power to the knee joint member.

In this case, it is sufficient if the active driving force is transmitted only in a specific section among the stance phase and swing phase during walking, and such a specific section may vary according to the pedestrian's walking situation. Hereinafter, it will be described by dividing into a case where the walking situation of a pedestrian is to walk on an upward slope and a case of climbing stairs.

Figure 9:
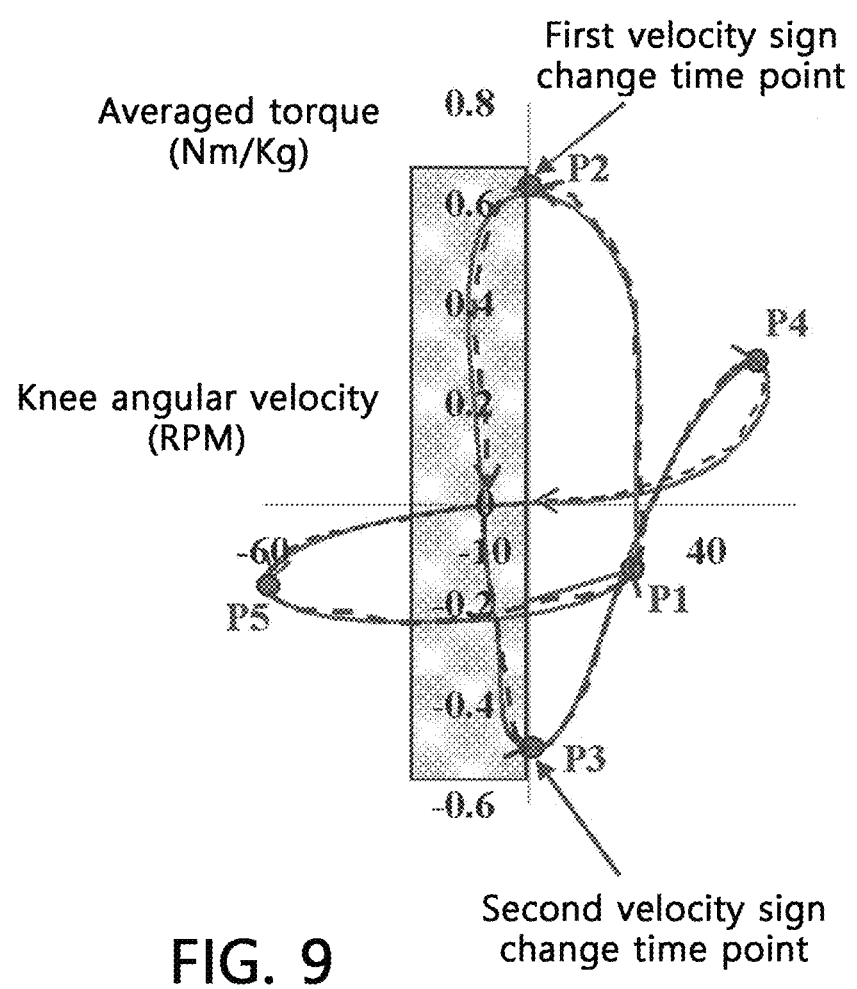
FIGS. 9 and 10 are graphs showing regions in which an active driving module is operated in the hybrid artificial limb device according to an exemplary embodiment of the present invention when a pedestrian walks on an upward slope.
Figure 10:
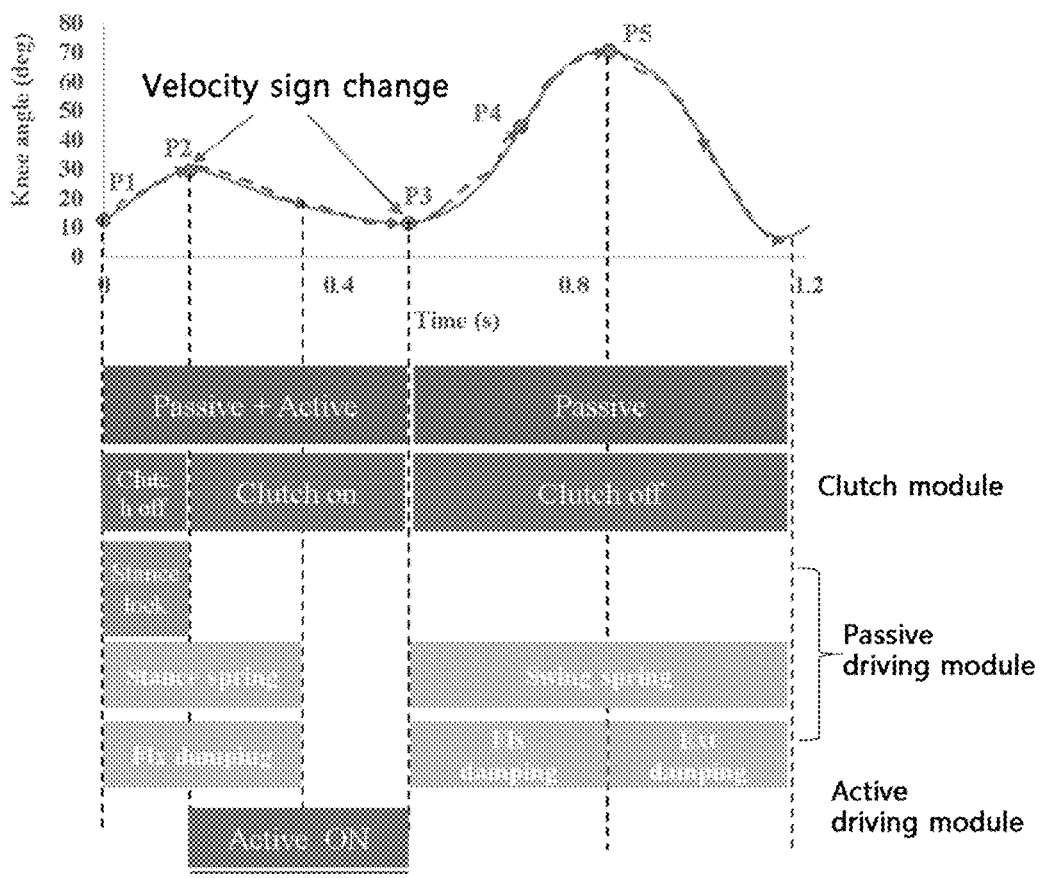

FIGS. 9 and 10 are graphs showing regions in which an active driving module is operated in the hybrid artificial limb device according to an exemplary embodiment of the present invention when a pedestrian walks on an upward slope. FIG. 9 is a graph where the x-axis shows the knee angular velocity (RPM), and the y-axis shows the averaged torque, and FIG. 10 is a graph where the x-axis shows time and the y-axis shows the knee angle.

Referring to FIGS. 9 and 10, when a pedestrian walks on a slope, the period in which the active driving force must be provided using the active driving module 14 may be defined as a section from a time point at which the knee angular velocity changes from positive to negative in the stance phase to a time point at which the knee angular velocity changes from negative to positive. As a result, it can be seen that the active torque is provided only in the case of the second and third quadrants where the knee angular velocity has a negative value, that is, the velocity in an extension direction. In this case, the reference value of the magnitude of the averaged torque at a time point of a first speed sign change and the reference value of the magnitude of the averaged torque at a time point of a second speed sign change may vary according to the settings.

In this case, in an exemplary embodiment of the present invention, when a pedestrian walks on a slope, the clutch module maintains the on state during the pedestrian's stance phase (P1 to P3), and an active driving force is provided during the aforementioned active driving force providing period (P2 to P3). In the section where the active driving force is not provided during the stance phase, only the passive driving force is transmitted by the hydraulic cylinder while the clutch module is on.

In other words, in the case of fast walking or an upward slope, it may be converted to the active mode, and in the case of normal walking on flat ground, the walking may be performed in the passive mode.

In addition, the clutch module is maintained in the off state in the swing phase section during periods other than the period in which the active driving force is provided such that only the passive driving force is provided.

In this case, referring to FIG. 9, the section in which the active driving force is provided is a section in which the velocity sign change occurs in the graph diagram where the x-axis represents the knee angular velocity and the y-axis represents the averaged torque, that is, it is a case from a time point P2 at which the graph enters the second quadrant from the first quadrant to a time point P3 at which the graph comes out of the third quadrant to the fourth quadrant. That is, in the graph, it can be seen from the graph that in the relationship graph between the knee angular velocity and the averaged torque, the period from the second quadrant through the third quadrant is a section in which the active driving force is required.

Such a section is a section in which two inflections are made among the stance phase section in the velocity versus knee angle curve of FIG. 10, and corresponds to a section from a point where the knee angle is the maximum to a point where the knee angle is the minimum during the stance phase. In terms of time, given that the time to go through one stance phase and swing phase is approximately 1.2 seconds, it may correspond to a section between 0.2 seconds and 0.5 seconds.

Meanwhile, in the case of running, sections for operating the passive driving module 12, the active driving module 14 and the clutch module 70 may be set similarly to walking on a slope.

Next, a section in which the active driving module 14 is operated when the pedestrian climbs the stairs will be described.

Figure 11:
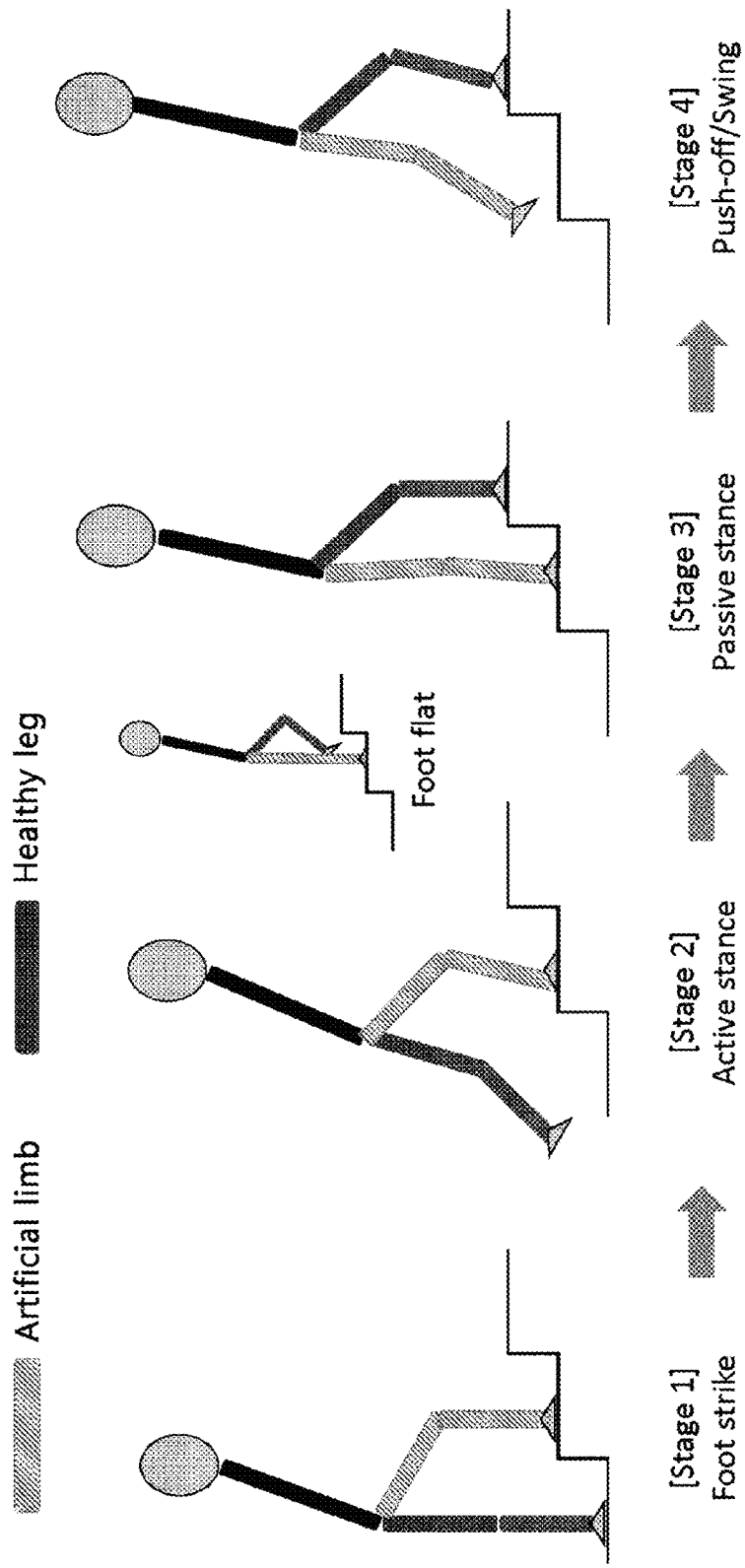
FIG. 11 is a diagram schematically illustrating the state of the artificial limb device in four states where a pedestrian climbs stairs.
Figure 12:
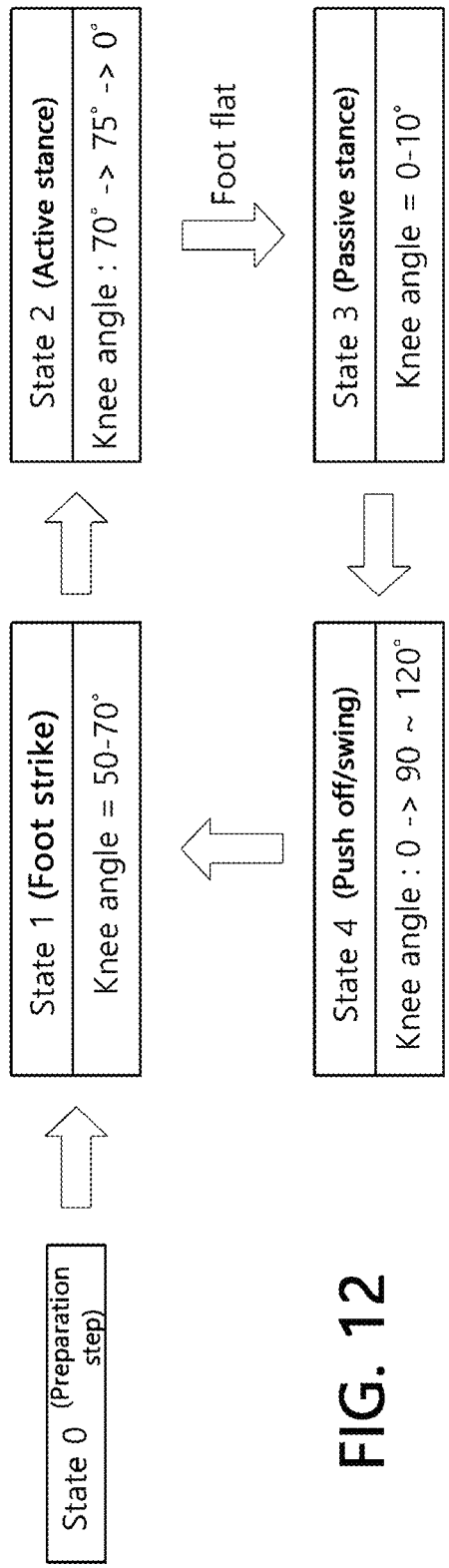
FIG. 12 is a diagram describing an operation and a knee angle corresponding to the four states where a pedestrian climbs stairs in FIG. 11, and the operational state of a hybrid artificial limb device corresponding thereto.
Figure 13:
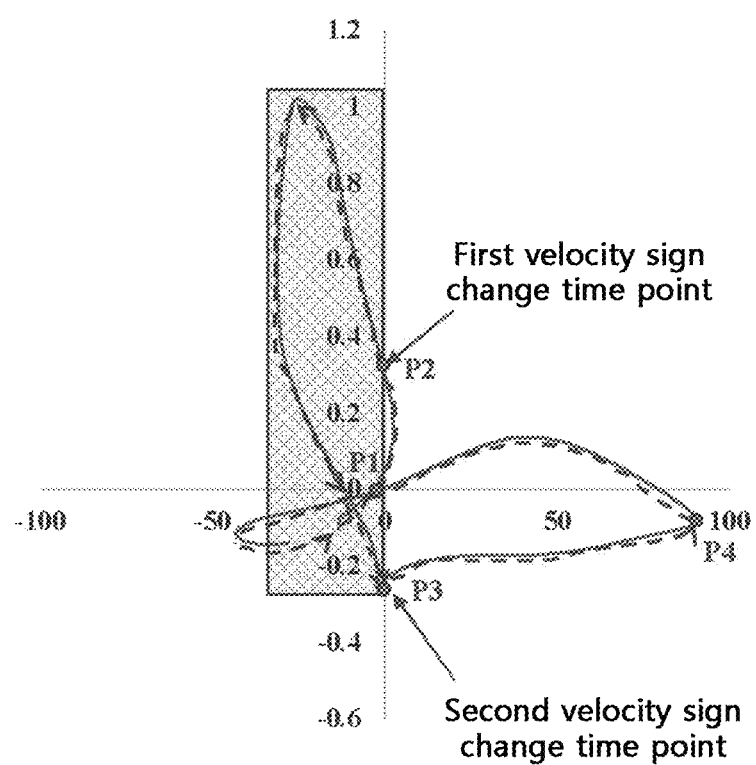
FIGS. 13 and 14 are graphs showing regions in which an active driving module is operated in the hybrid artificial limb device according to an exemplary embodiment of the present invention, when a pedestrian climbs stairs.
Figure 14:
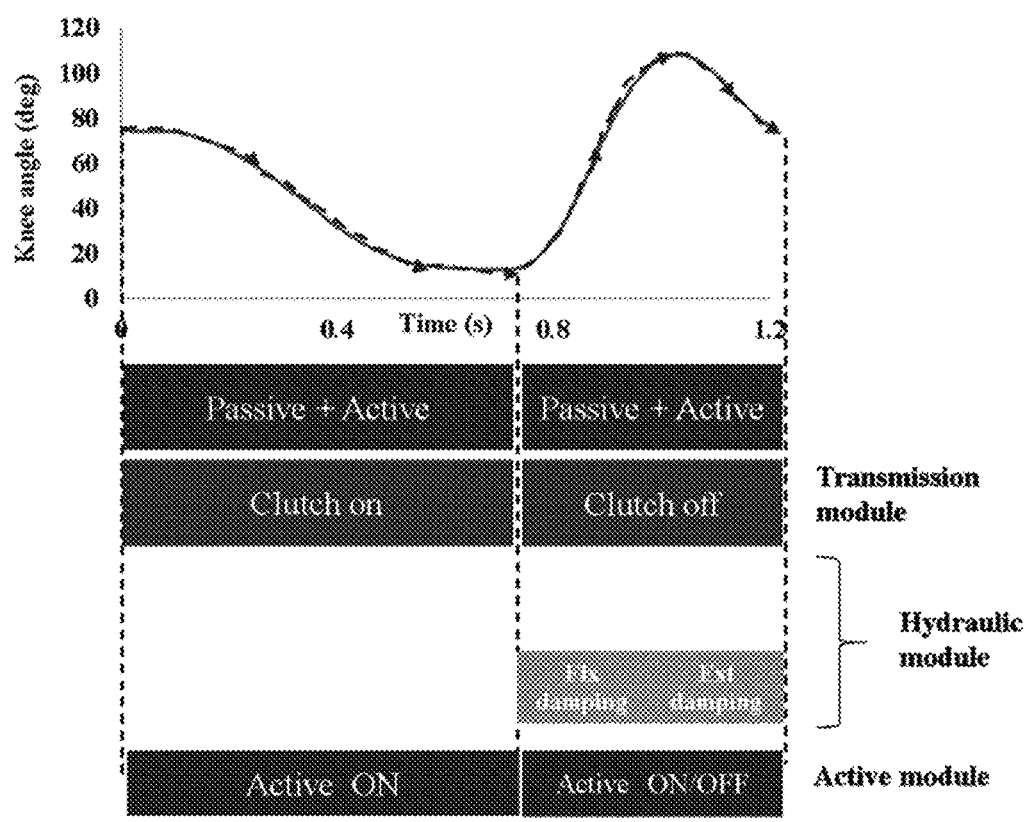

FIG. 11 is a diagram schematically illustrating the state of the artificial limb device in four states where a pedestrian climbs stairs. FIG. 12 is a diagram describing an operation and a knee angle corresponding to the four states where a pedestrian climbs stairs in FIG. 11, and the operational state of a hybrid artificial limb device corresponding thereto. FIGS. 13 and 14 are graphs showing regions in which an active driving module is operated in the hybrid artificial limb device according to an exemplary embodiment of the present invention, when a pedestrian climbs stairs. In FIG. 13, in the case of the knee angular velocity of the x-axis, a positive value indicates a bending direction speed, and a negative value indicates an extension direction speed. In the case of the averaged torque of the y-axis, a positive value indicates an extension direction torque, and a negative value indicates a flexion direction torque. In FIG. 14, the x-axis represents one cycle time of the human gait cycle period, and the y-axis represents the relative knee joint angle, and a positive value represents the relative flexion angle of the shin compared to the femoral part.

In the pedestrian's climbing the stairs, the state of the pedestrian may be largely divided into five steps.

The first step is a preparation step (state 0). In the preparation step, a pedestrian waits with both feet in front of stairs, and generates a trigger signal to climb the stairs. In this case, if a trigger signal indicating that the pedestrian climbs the stairs is not generated, the signal indicating that the pedestrian will climb the stairs may not be sensed only by the sensor of the artificial limb device. The trigger signal for climbing the stairs may vary depending on the settings, and for example, a specific action, such as tapping the floor surface with a heel twice, may be such a trigger signal. The trigger signal may be variously set according to the settings.

The second step is an artificial foot landing step (state 1). In the artificial foot landing step, the artificial limb is lifted up the stairs to land on the first stair. In this case, the knee angle is about 50 to 70 degrees, and the artificial foot landing step may be performed in a passive state in which no power is transmitted to the knee joint.

The third step is an active stance step (state 2). In the active stance step, the center of gravity is slightly shifted forward, and the knee is slightly bent and then extended while the healthy leg up. In this case, the clutch module 70 should be maintained in the on state, and the active driving power in an extension direction should be provided using the active driving module 14. In addition, the passive driving force in a bending direction should also act in preparation for a situation where power is insufficient such that it is rotated only in an extension direction without bending the knee. In this case, the knee angle is slightly bent from 70 degrees to 75 degrees, followed by completely straightening to 0 degrees.

The fourth step is a passive stance step (state 3). In this case, with the affected knee slightly bent or fully extended, the uncomfortable side swings to the next stair. In this state, a passive driving force is used and the clutch module is maintained in the off state. In this case, the knee angle is 0 degrees.

The fifth step is a push off/swing step (state 4). In this case, the affected knee is slightly bent in order to move the weight toward the uncomfortable side, and the knee on the artificial limb side is rotated largely so as to generate inertia to lift the foot on the artificial limb side above the stairs. In this step, passive driving is basically performed, but depending on the weight of the artificial limb and the ability of the disabled person with amputation, an active driving force and a passive driving force may be used simultaneously. It may proceed from the push-off/swing step to the artificial foot landing step, which is the second step, and the process of climbing the next stairs may be repeated. In this case, the knee angle is bent from 0 degrees to 90 degrees to 120 degrees.

Even in the process of climbing the stairs, similar to walking on a general slope, the clutch module is maintained in the on state during the stance phase section, and the clutch module is maintained in the off state during the swing phase section.

In this case, the condition in which the active driving module 14 operates when the pedestrian climbs the stairs is the moment when the knee angular velocity changes from positive to negative after the generation of the stair climbing trigger signal, and the condition in which the active driving module is released is until the moment when the knee angular velocity changes from negative to positive.

Further, in the graph of FIG. 13 where the x-axis represents the knee angular velocity and the y-axis represents the averaged torque, the section in which the active driving force is provided is a case from a time point P2 at which the velocity sign change occurs, that is, when the graph enters the second quadrant from the first quadrant, to a time point P3 at which the graph comes out from the third quadrant to the fourth quadrant. That is, in the relationship graph between the knee angular velocity and the averaged torque, the period from the second quadrant through the third quadrant is a section in which the active driving force is required in the graph.

In this case, in the process of climbing the stairs, the clutch-on section of the stance phase may be longer than walking on a slope, and in terms of time, if the entire section of walking up once is carried out for 1.2 seconds, the active driving module is operated while the clutch is on for the section from 0 to 0.7 seconds to provide an active driving force.

Meanwhile, depending on the height of the stairs, both of the passive mode and active mode may be utilized. In addition, impedance control may be performed in relation to the active module, and a complex sensor may be applied to determine a transition event/force.

The hybrid-type artificial limb device according to an exemplary embodiment of the present invention may specify a section in which the active driving module 14 should be used, for example, a section in which the active driving module 14 is operated while walking on a slope and a section in which the active driving module 14 is operated while climbing the stairs as described above to provide an active driving force, thereby minimizing the energy consumption section, and since it can provide a pedestrian with an appropriate force necessary for the pedestrian in the corresponding section, it is possible to efficiently use the hybrid-type artificial limb device for a long period of time.

In this way, since the hybrid-type artificial limb device that operates the active driving module only when the active driving is required efficiently uses energy, the size of the battery installed in the artificial limb device may be reduced, thereby reducing the weight of the hybrid-type artificial limb device, and accordingly, it is possible to provide a compact hybrid-type artificial limb device.

In addition, the hybrid-type artificial limb device according to an exemplary embodiment of the present invention provides power using the active driving module only in at least some section during the stance phase, even when the active driving module should be used, and minimizes the use of the battery by using the passive driving module in the swing phase section, and thus, it is possible to maximize the battery usage time.

Although an exemplary embodiment of the present invention has been described above, the spirit of the present invention is not limited to the exemplary embodiment presented in the present specification, and those skilled in the art who understand the spirit of the present invention will be able to easily suggest other exemplary embodiments by modifying, changing, deleting or adding components within the scope of the same spirit, but this is also said to be within the scope of the present invention.

The invention claimed is:

1. A hybrid-type artificial limb device, comprising:
a joint upper side connection member positioned at the upper side of a knee;
a knee joint member connected to the joint upper side connection member; and
a frame coupled to the knee joint member to be able to perform a pivot rotation, and forming a femoral part, and
the hybrid-type artificial limb device further comprises a passive driving module which includes a hydraulic cylinder connected to the knee joint member, so as to transfer passive power to the knee joint member, and an active driving module which is coupled to the knee joint member so as to transfer active power to the knee joint member,
wherein the active driving module comprises:
a first pulley coupled to the knee joint member;
a second pulley rotatably installed on one end of the frame in a direction away from the knee joint member;
a driving cable operatively connecting the first pulley and the second pulley;
a driving motor for actively operating the driving cable; and
a clutch module connected between the cable and the driving motor so as to selectively transmit power of the driving motor to the driving cable,
wherein when the frame performs a pivot rotation about the knee joint member, the passive power from the passive driving module and the active power from the active driving module may be selectively or simultaneously provided to the knee joint member,
wherein one end of the hydraulic cylinder in an extension direction is operatively coupled to the knee joint member at a location on an outer peripheral side of the knee joint member,
wherein the other end of the hydraulic cylinder in an extension direction is connected to one end side of the frame in a direction away from the knee joint member,
wherein when the power of the driving motor is connected to the cable by the clutch module in a transferable state, the clutch module is moveable together with the cable,
wherein the frame is provided with a guide member for guiding the movement of the clutch module when the clutch module moves together with the cable,
wherein the clutch module includes a first portion coupled toward the driving cable and a second portion coupled to the guide member, and
wherein the first portion and the second portion is formed to be mutually fastened or separated.

2. The hybrid-type artificial limb device of claim 1, wherein the first pulley is arranged concentrically with the rotation axis of the knee joint member.

3. The hybrid-type artificial limb device of claim 1, wherein the first pulley is formed integrally with the knee joint member.

4. The hybrid-type artificial limb device of claim 1, wherein the first pulley is operatively coupled to the knee joint member so as to be simultaneously rotatable.

5. The hybrid-type artificial limb device of claim 1, wherein the hydraulic cylinder of the passive driving module is disposed parallel to a plane on which the driving cable of the active driving module operates.

6. The hybrid-type artificial limb device of claim 1, wherein when the active driving module is connected to the cable by the clutch module in a state where the power of the driving motor is transferable, the driving motor moves the guide member such that the clutch module connected to the guide member and the cable are formed to move together, and the pivot rotation of the frame about the knee joint member is made according to the movement of the cable.

7. A method for controlling a hybrid-type artificial limb device according to claim 1, the hybrid-type artificial limb device comprising a joint upper side connection member positioned at the upper side of a knee; a knee joint member connected to the joint upper side connection member; and a frame coupled to the knee joint member to be able to perform a pivot rotation, and forming a femoral part, and further comprising a passive driving module and an active driving module connected to the knee joint member,
wherein under a first walking condition of a user who is equipped with the artificial limb device, the user walks using the passive driving module that transmits passive power to the knee joint member, and
wherein under a second walking condition of a user who is equipped with the artificial limb device, the user walks using the active driving module that is connected to the knee joint member.

8. The method of claim 7, wherein the first walking condition of the user is to walk on flat ground with an inclination angle which is less than a predetermined angle.

9. The method of claim 7, wherein under the first walking condition, the active driving module is controlled to cut off power transmission to the knee joint member, when walking using the passive driving module.

10. The method of claim 7, wherein the second walking condition of the user is to walk on an incline with an inclination angle which is greater than or equal to a predetermined angle, run or climb stairs.

11. The method of claim 7, wherein under the second walking condition of the user, the active driving module is mechanically controlled such that power is transmitted to the knee joint member only when walking using the active driving module.

12. The method of claim 11, wherein a condition in which the active driving module operates when walking on an incline in the second walking condition of the user is when a knee angular velocity changes from positive to negative, and
wherein a condition in which the active driving module is released when walking on an incline in the second walking condition of the user is when a knee angular velocity changes from negative to positive.

13. The method of claim 11, wherein a condition in which the active driving module operates when climbing stairs in the second walking condition of the user is when a knee angular velocity changes from positive to negative, and wherein a condition in which the active driving module is released when climbing stairs in the second walking condition of the user is when a knee angular velocity changes from negative to positive.

14. The method of claim 7, wherein the active driving module and the passive driving module operate together under the second walking condition.

15. The method of claim 7, wherein the active driving module operates within a stance phase range of the user under the second walking condition of the user.

* * * * *